US00PP08009P

United States Patent [19]

VandenBerg

[11] Patent Number: Plant 8,009

[45] Date of Patent: Oct. 20, 1992

[54] CHRYSANTHEMUM PLANT NAMED BALADA

[76] Inventor: Cornelis P. VandenBerg, 230 Winham St., Salinas, Calif. 93901

[21] Appl. No.: 668,604

[22] Filed: Mar. 13, 1991

[51] Int. Cl.[5] ..... A01H 5/00

[52] U.S. Cl. ..... Plt./74.1

[58] Field of Search ..... Plt./74, 74.1, 82.2, Plt./82.3

*Primary Examiner*—Howard J. Locker

[57] ABSTRACT

A Chrysanthemum plant named Balada particularly characterized by its flat capitulum form; daisy capitulum type; orange-bronze ray floret color; diameter across face of capitulum of 76 to 89 mm when fully opened, when grown as a single stem spray cut mum; flowering response in Salinas, Calif. under normal temperatures of 50 to 54 days after start of short days, and in Bogota, Colombia under temperatures of minimum 6.4 degrees Celsius night and maximum 29 degrees Celsius day of 63 to 72 days; plant height of 76 to 94 cm when grown in Salinas with 6 to 14 long days prior to start of short days, and 102 to 117 cm when grown in Bogota with 14 to 17 long days prior to start of short days; peduncle length of the first lateral at flowering after removing the apical bud without growth regulator applications of 10 to 15 cm when grown in Salinas, and 10 to 20 cm when grown in Bogota; peduncle length of the fourth lateral at flowering of 13 to 20 cm when in Salinas, and 15 to 23 cm when grown in Bogota; and excellent tolerance to low night temperatures for bud initiation and flower development.

3 Drawing Sheets

The present invention comprises a new and distinct cultivar of Chrysanthemum, botanically known as *Dendranthema grandiflora,* and referred to by the cultivar name Balada.

Balada, identified as 1907 (87-434008), was originated from a cross made by Cornelis P. VandenBerg in a controlled breeding program in Salinas, Calif., in 1986.

The female parent of Balada was an unnamed seedling identified as 6826 (84-187105), and described as a pink flat daisy cut spray mum. When grown in Salinas, Calif. 6826 (84-187015) has a flowering response to short days of 53 to 67 days, a height of 64 to 99 cm 0 to 15 long days prior to start of short days, a peduncle length of the first lateral of 10 to 20 cm and of the fourth lateral of 13 to 23 cm, and a flower diameter of 63 mm. When grown in Bogota, Colombia, 6826 (84- 187015) has a flowering response of 70 to 74 days, a height of 107 to 117 cm with 14 to 21 long days prior to start of short days, and a peduncle length of the first lateral of 15 to 20 cm and of the fourth lateral of 18 to 20 cm. No flower diameter was recorded in Colombia. 6826 (84-187015) was discarded from all programs on Oct. 19, 1987.

The male parent of Balada was an unnamed seedling identified as 5971 (82-J20070), and described as a bronze flat daisy spray cut mum. When grown in Salinas, Calif., 5971 (82-J20070) has a flowering response to short days of 53 to 64 days, a height of 66 to 99 cm with 11 to 14 long days prior to start of short days, a peduncle length of the first lateral of 8 to 10 cm and of the fourth lateral of 10 to 15 cm, and a flower diameter of 70 to 76 mm. When grown in Bogota, Colombia, 5971 (82-J20070) has a flowering response to short days of 70 to 90 days, a height of 94 to 119 cm with 7 to 14 long days prior to start of short days, and a peduncle length of the first lateral of 15 to 23 cm and of the fourth lateral of 23 cm. No flower diamter was recorded in Colombia, 5971 (82-J20070) was discarded from all programs on May 12, 1986.

Balada was discovered and selected as one flowering plant within the progeny of the stated cross by Cornelis P. VandenBerg in November of 1987, in a controlled environment in Salinas, Calif.

The first act of asexual reproduction of Balada was accomplished when vegetative cuttings were taken from the initial selection in January of 1988 in a controlled environment in Salinas, Calif., by technicians working under the supervision of Cornelis P. VandenBerg.

Horticultural examination of controlled flowerings of successive plantings has shown that the unique combination of characteristics as herein disclosed for Balada are firmly fixed and are retained through successive generations of asexual reproduction.

Balada has not been observed under all possible environmental conditions. The phenotype may vary significantly with variations in environment such as temperature, light intensity and daylength.

The following observations, measurements and comparisons describe plants grown in Salinas, Calif. and Bogota, Colombia, under greenhouse conditions which approximate those generally used in commercial greenhouse practice. The low temperature tolerance was determined in repeated flowerings in Bogota, Colombia, with an average minimum low night temperature inside the greenhouse in Bogota during our trials ranging from 6.3 to 10.0 degrees Celsius.

The following traits have been repeatedly observed and are determined to be basic characteristics of Balada, which, in combination, distinguish this Chrysanthemum as a new and distinct cultivar:

1. Flat capitulum form.
2. Daisy capitulum type.
3. Orange-bronze ray floret color.
4. Diameter across face of capitulum of 76 to 89 mm when fully opened, when grown as a single stem spray cut mum.
5. Flowering response in Salinas under normal temperatures is 50 to b 54 days after start of short days. Flowering response in Bogota, Colombia under temperatures of minimum 6.3 degrees Celsius night and maximum 29 degrees Celsius day is 63 to 72 days.

6. Plant height is 76 to 94 cm when grown in Salinas with 6 to 14 long days prior to start of short days; height is 102 to 117 cm when grown in Bogota with 14 to 17 long days prior to start of short days.

7. Peduncle length of the first lateral at flowering after removing the apical bud without growth regulator applications is 10 to 15 cm when grown in Salinas, and 10 to 20 cm when grown in Bogota. Peduncle length of the fourth lateral at flowering is 13 to 20 cm when grown in Salinas, and 15 to 23 cm when grown in Bogota.

8. Excellent tolerance to low night temperatures for bud initiation and flower development.

The accompanying photographic drawings show typical inflorescence and leaf characteristics of Balada, with the colors being as nearly true as possible with illustrations of this type.

Sheet 1 is a color photograph of Balada grown as a single stem spray cut mum.

Sheet 2 is a black and white photograph of three views of the infloresence of Balada.

Sheet 3 is a black and white photograph showing the upper and under sides of the leaves of Balada at three stages of development (mature, intermediate and immature). In sheets 2 and 3 a measuring tape in centimeters has been included.

Of the commercial cultivars know to the inventor, the most similar in comparison to Balada is the cultivar Paleto, disclosed in U.S. Plant Pat. No. 6,903. Reference is made to attached Chart A, which compares certain characteristics of Balada to the same characteristics of Paleto.

Similar traits are ray floret color, capitulum form and type, spray formation and low night temperature tolerance. Plant height is comparable for both cultivars in Colombia, but plant height of Balada is shorter than the height of Paleto when grown in Salinas. Balada has a larger flower diameter, a faster flowering response in both trial locations, and shorter peduncle length when compared with Paleto.

When compared with both parents, Balada has a larger flower diameter and a faster flowering response to short days.

In the following description color references are made to The Royal Horticultural Society Colour Chart. The color values were determined on plant material grown as a single stem spray cut mum in Salinas, Calif. on Jun. 20, 1990.

Classification:

*Botanical.*—*Dendranthema grandiflora* cv Balada.

*Commercial.*—Daisy spray cut mum.

INFLORESCENCE

A. Capitulum:

*Form.*—Flat.

*Type.*—Daisy.

*Diameter across face.*—76 to 89 mm when fully opened.

B. Corolla of ray florets:

*Color (general tonality from a distance of three meters).*—Orange-bronze.

*Color (upper surface).*—162A, overlaid with 168B to 168C. Immature flowers heavily overlaid.

*Color (under surface).*—163D, slightly overlaid and streaked with 168B.

*Shape.*—Straight, base slightly concave, mature petal tips slightly convex. Cross section straight, slightly ribbed.

C. Corolla of disc florets:

*Color (mature).*—12A.

*Color (immature).*—12A, center slightly overlaid with 144B.

D. Reproductive organs:

*Androecium.*—Present on disc florets only; moderate pollen.

*Gynoecium.*—Present on both ray and disc florets.

PLANT

A. General appearance:

*Height.*—76 to 94 cm when grown in Salinas with 6–14 long days prior to start of short days, and 102 to 117 cm when grown in Bogota with 14 to 17 long days prior to start of short days.

B. Foliage:

*Color (upper surface).*—147A.

*color (under surface).*—147B.

*Shape.*—See photograph.

CHART A

COMPARISON OF BALADA AND PALETO

| Characteristic | Balada | Paleto |
|---|---|---|
| Ray floret color | Orange-bronze | Orange-bronze |
| Capitulum form and type | Flat daisy | Flat daisy |
| Diameter across face of capitulum | 76 to 89 mm | 70 to 80 mm |
| Flowering response | | |
| in Salinas | 50 to 54 days | 51 to 60 days |
| in Bogota | 63 to 72 days | 70 to 80 days |
| Plant height: | | |
| 6–14 long days Salinas | 76 to 94 cm | 91 to 102 cm |
| 14–17 long days Bogota | 102 to 117 cm | 107 to 112 cm |
| Peduncle length: | | |
| 1st lateral Salinas | 10 to 15 cm | 10 to 18 cm |
| 4th lateral Salinas | 13 to 20 cm | 18 to 23 cm |
| 1st lateral Bogota | 10 to 20 cm | 15 to 23 cm |
| 4th lateral Bogota | 15 to 23 cm | 20 to 23 cm |
| Spray formation | Terminal | Terminal |
| Low night temperature tolerance | Excellent | Excellent |

COMPARISONS MADE OF PLANTS GROWN AS SINGLE STEM SPRAY CUT MUMS IN SALINAS, CALIFORNIA AND IN BOGOTA, COLOMBIA

I claim:

1. A new and distinct Chrysanthemum plant named Balada, as described and illustrated.

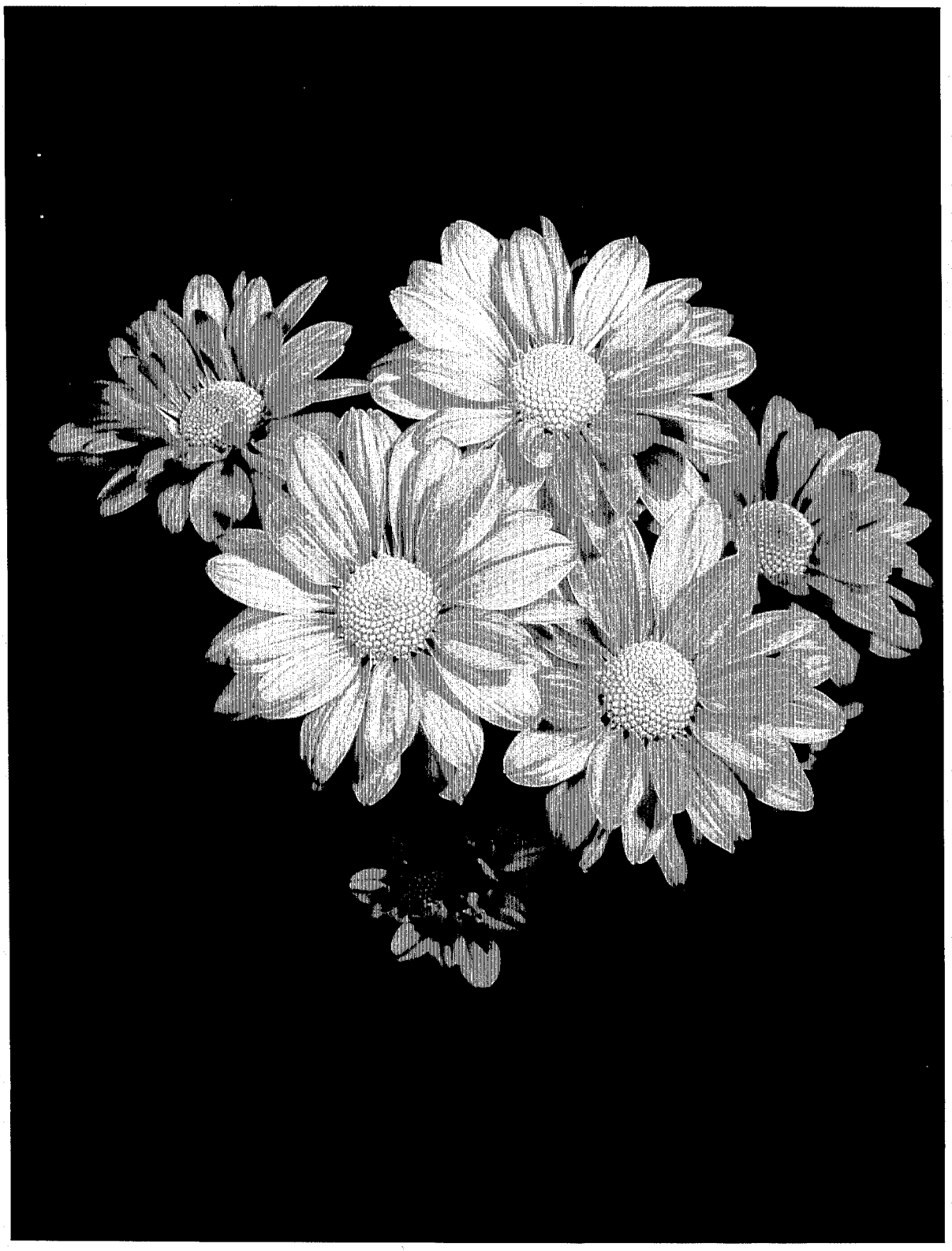

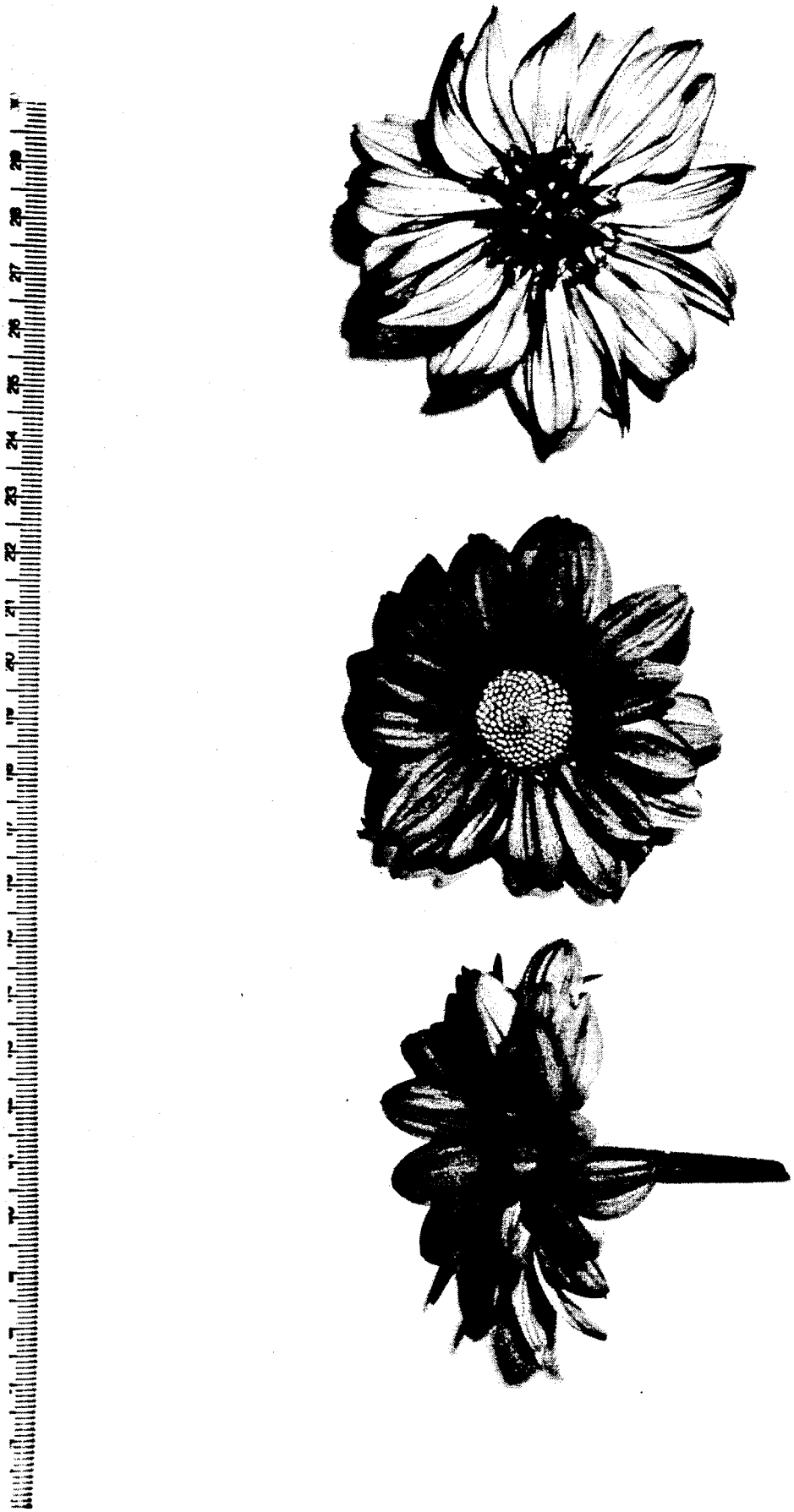

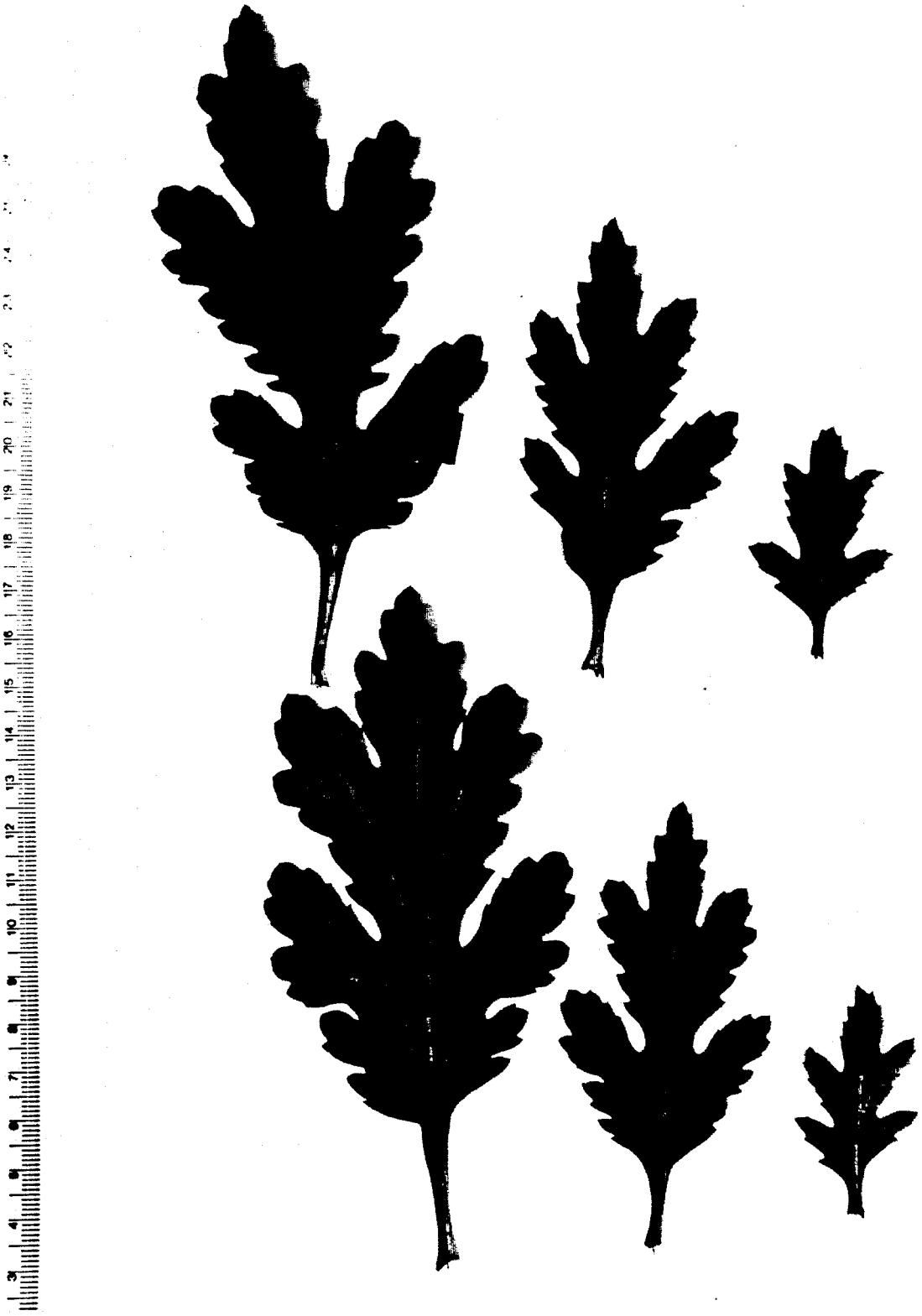

* * * * *